United States Patent [19]

Singh et al.

[11] Patent Number: 5,648,611
[45] Date of Patent: Jul. 15, 1997

[54] PROCESS FOR MEASURING THE CASE DEPTH OF CASE-CARBURIZED STEEL

[75] Inventors: Surrendra Singh; Rosendo Fuquen; David R. Leeper, all of Stark, Ohio

[73] Assignee: The Timken Company, Canton, Ohio

[21] Appl. No.: 519,989

[22] Filed: Aug. 28, 1995

Related U.S. Application Data

[63] Continuation-in-part of Ser. No. 171,815, Dec. 22, 1993, abandoned.
[51] Int. Cl.$^6$ ................................................. G01N 29/00
[52] U.S. Cl. ............................ 73/598; 73/629; 73/597
[58] Field of Search ............................ 73/598, 597, 629, 73/643, 622; 148/902

[56] References Cited

U.S. PATENT DOCUMENTS

| | | | |
|---|---|---|---|
| 4,098,129 | 7/1978 | Deblaere et al. | 73/599 |
| 4,184,374 | 1/1980 | Thompson et al. | 73/640 |
| 4,457,174 | 7/1984 | Bar-Cohen | 73/598 |
| 5,031,457 | 7/1991 | Kline | 73/598 |
| 5,085,082 | 2/1992 | Cantor et al. | 73/622 |
| 5,299,458 | 4/1994 | Clark | 73/597 |

FOREIGN PATENT DOCUMENTS

280582A  1/1990  Germany .

OTHER PUBLICATIONS

Tittmann, et al Proc. 9th Symposium on NDE Measurement of Physical Property Gradients With Elastic Surface Wave Dispersion Apr. 25–27, 1973 pp. 20–28.
Rivenez, etal Nondestructive Determination of Hardening Depths with Ultrasonic Surface Waves pp. 373–380.
Rivenez, et al Cetim Nondestructive Determination of Hardening Depths With Ultrasonic Surface Waves pp. 1–9.
Non Destructive Measuring of Heat Treated Case Depths pp. 1–17.
Rivenez, et al Heat Treatment of Metals 1988.2 Non–destructive Testing and Assessment of Hardness Gradients pp. 29–33.
Industrial Heating Advances in NDT Impacting Thermal Processing Aug. 1992 pp. 8, 10.
S. Singh, et al 1991 Spring Conference Oakland CA Effects of Carbon Level and Microstructure on Ultrasonic Velocity in Steels 1991 pp. 140–142.
Thompson 1977 Ultrasonics Symposium Proc Noncontact Transducers pp. 74–83.
Halmshaw, Metallurgy and Materials Science Series Non–destructive Testing 1987 pp. 109–123 132–151.
Thompson, et al Proc. 9th Symposium on NDE Noncontact Ultrasonic Surface Wave Transducers and Their Application to Nondestructive Testing Apr. 25–27, 1973 pp. 6–9, 12–19.
Thompson Ultrasonics Symposium Electromagnetic, Noncontact Transducers 1973 pp. 385–392.
Jakel Magnetic and Electromagnetic Methods for Nondestructive Testing of the Depth of Hardened or Case–Hardened Semifinished and Finished Products 1966 pp. 1–24.
Alers Measurement of Hardness vs. Depth Contours by Ultrasonic Velocity pp. 85–92.
Starzynski J. Pure Ultrason. vol. 10, No. 3 Estimation of elastic properties profile from Rayleigh's wave velocity dispersion 1988 pp. 49–52.

(List continued on next page.)

*Primary Examiner*—Hezron E. Williams
*Assistant Examiner*—Helen C. Kwok
*Attorney, Agent, or Firm*—Polster, Lieder, Woodruff & Lucchesi, L.C.

[57] ABSTRACT

The depth of a case on a specimen of case-carburized steel is measured by launching an acoustic wave along the surface of the specimen such that the wave passes through the case, and measuring the velocity of that wave within the specimen. From an existing correlation of velocity and case depth for the very same core steel as the specimen, one finds the case depth which corresponds to the measured velocity, and that is the case depth of the specimen.

12 Claims, 3 Drawing Sheets

OTHER PUBLICATIONS

Malinka Radiation and Reception of Ultrasonic Vibrations at a Given Angle Using an Electromagnetoacoustic Method 4 Pages.

Butenko, et al Non–Destructive Testing Electromagneto–acoustic non–destructive testing in the Soviet Union Jun. 1972 pp. 154–159.

Maxfield, et al Proc. 10th Symposium on NDE Electromagnetic Acoustic Wave Transducers Their Operation and Mode Patterns Apr. 23–25, 1975 pp. 44–62.

Kuznetsov An Electromagnetic Method of Testing Hardened Surfaces for Quality pp. 1–7 FIGS. 1–5.

Pavlov Electrical Method of Measuring Carburized Case Depth and Thickness of NonMagnetic Electrodeposited Coatings 1958 pp. 1–4 FIGS. 1–5.

Jakel Magnetic and Electromagnetic Methods for the Nondestructive Testing of the Depth of Hardening of Case–Hardened Semi–finished and Finished Products Part II—Studies and Test Results 1966 pp. 1–14 FIGS. 1–18.

Thompson Review of Progess in Quantitative Nondestructive Evaluation —vol. 3A 1984 pp. 1221–1228.

Weston–Bartholomew Int'l Advances In Nondestructive Testing Use of the Ultrasonic Goniometer to Measure Depth of Case Hardening (The Corner Reflection Method) 1979 pp. 111–123.

Palanisamy, et al Eddy Current Sizing of Case Depth in Bearing Components pp. 363–372.

Hoeprich U. of Cincinnati, thesis Ultrasonic Measurement of Case Depth in Case Hardened Steel 1971 ii–iv; pp. 1–48.

Good Ultrasonic Measurement of Case Depth in Case Hardened Steels 1982 pp. 1–53 Title page and abstract.

PROCESS FOR MEASURING THE CASE DEPTH OF CASE-CARBURIZED STEEL

RELATED APPLICATION

This application is a continuation-in-part of U.S. patent application Ser. No. 08/171,815 of Surrendra Singh, Rosendo Fuquen and David Leeper entitled Process for Measuring the Case Depth of Case-Hardened Steel, filed Dec. 22, 1993, now abandoned.

BACKGROUND OF THE INVENTION

This invention relates in general to case-hardened steel and more particularly to a process for determining the case depth of case-caburized steel.

Low carbon steel has good ductility and as such will withstand bending stresses and impacts quite well. However, it cannot be hardened to the extent required for wear-resistant surfaces. High carbon steel, on the other hand, by reason of its higher carbon content, will transform into a large proportion martensite when subjected to a proper heat treatment—and martensite is the hardest structure that can be obtained from steel in any appreciable amount. A properly hardened high carbon steel resists fatigue, wear, indentation and abrasion, and as such provides a good wear surface. But high carbon hardened steels are somewhat brittle and certainly not as tough as low carbon steels. Case-carburizing enables ductile low carbon steel to acquire a hard surface or case which resists fatigue, wear, indentations and abrasion. Thus, case-carburized steel possesses the attributes of both low carbon steel in the core region and properly treated high carbon steel in the case region.

Iron at elevated temperatures on the order of 1350° F. to 1850° F. exhibits an affinity for carbon, so when a workpiece formed from low carbon steel is heated in a carbon-rich atmosphere, the carbon diffuses into the steel. The extent of the diffusion depends on the constituency of the carbon-rich atmosphere, which is often carbon monoxide and methane, the temperature to which the steel is heated, and the time it remains in the carbon-rich atmosphere. In effect, the region at the surface of the steel workpiece transforms into high carbon steel. Thus, when the workpiece is heated above the temperature at which the carbon-enriched portion becomes austenite, and then quenched, the carbon-enriched portion to a large measure transforms into martensite and becomes a hard case, but the remaining portion, called the core, remains relatively soft and ductile.

One of the more important applications of case-carburizing resides in the manufacture of roller bearings, particularly tapered roller bearings. The races of these bearings must withstand impact stresses and thus should have the ductility of low or medium carbon steel. However, the surfaces of the races, particularly the surfaces which the rollers contact, should be hard to resist wear, indentations and abrasion. Case-carburizing further imparts residual compressive stresses to the cases of the ring-shaped races and this enables the races, along their raceways to better withstand bending fatigue and to inhibit the propagation of cracks from nicks.

Of course, the case cannot be too shallow; it must have reasonable depth to perform its function. But measuring case depth has heretofore been a time-consuming procedure requiring destruction of carburized specimens—and one should know whether the case of a workpiece meets minimum requirements. Actually, no distinct interface exists between the case and the core. Instead, the amount of carbon diffused into the steel simply decreases with depth to the point that the carbon content remains constant at that of the core. Typically, metallurgists use the depth at which a selected carbon content, such as 0.5% carbon, exists as the depth of the case. With the term "case depth" so defined, two procedures have been developed for ascertaining it—at least in connection with ring-like workpieces such as bearing races—namely, the Ms (Martensite start) procedure and carbon gradient procedure. Both require destruction of a specimen and are practiced only on carbon cut rings which are placed in the carburizing furnace with actual workpieces, the assumption being that the carbon cut rings, which are formed from the same steel as the workpieces, will absorb as much carbon as those workpieces and hence acquire a case of the same depth. Apart from being destructive, the tests are also very time-consuming.

The Ms procedure relies on the capacity of steel, when heated to austenite and subsequently quenched, to form martensite which has a well-defined crystalline structure that is readily apparent under a microscope. Actually, the transformation from austenite to martensite begins at a so-called Ms (Martensite start) temperature and that temperature varies with carbon content. For example, the Ms temperature for steel having 0.8% carbon by weight is lower than the Ms temperature for steel having 0.5% carbon by weight. Thus, when the carbon cut ring is heated above its austenizing temperature and then quenched to the Ms temperature for 0.5% carbon, all steel within the case containing that proportion of carbon or less transforms into martensite. The ring remains at the Ms temperature for a short period of time and then is quenched in water. With this quench the steel which has more than 0.5% carbon, becomes "fresh" martensite. Once the ring is cut and the cross-sectional surface polished and etched, the boundary between the original martensite and the fresh martensite stands out quite clearly. One can of course measure from that boundary to the surface of the ring to obtain the case depth, that is the depth at which 0.5% carbon concentration exists. However, this procedure is subjective in nature.

In the carbon gradient procedure, the carbon cut ring is secured in the chuck of a lathe and chips are removed at various depths, with the depth of each chip being recorded. The chips are then subjected to chemical analysis for carbon content. The depth recorded for the chip which shows 0.5% carbon content represents the case depth.

To be sure, others have experimented with nondestructive procedures for determining case depth, but have met with only limited success and no industry-wide procedure has evolved from any of the work. For example, some have attempted to measure the back scattering from acoustic waves sent into a workpiece, but the absence of a well-defined boundary between the case and core in case-hardened steel prevents this technique from being of much value. Others have used surface waves at various frequencies to plot dispersion curves for different case depths, but these efforts have not resulted in a meaningful testing procedure suitable for industry. The objective of these studies has been to study the depth profiles of elastic properties and hardness below the surface, not to measure case depth in a case-carburized specimen. Besides, the problem resides in the transducers used to impart the wave and detect its presence, for they, being piezoelectric devices, must be physically coupled to the workpiece under study.

The present invention resides in measuring the velocity of an acoustic wave which passes through the case of a specimen, and comparing that velocity with an existing correlation of velocity and case depth to determine the case depth corresponding to that velocity, which is the case depth of the specimen.

DESCRIPTION OF THE DRAWINGS

In the accompanying drawings which form part of the specification and wherein like numerals and letters refer to like parts wherever they occur.

DETAILED DESCRIPTION

The process of the present invention is useful for determining the case depth of case-hardened specimens, preferably specimens which take the form of rings, with the case being derived from case-carburizing and subsequent heat treatment and quenching. The process leaves the specimen intact, that is to say, it does not destroy the specimen.

Figure 1:
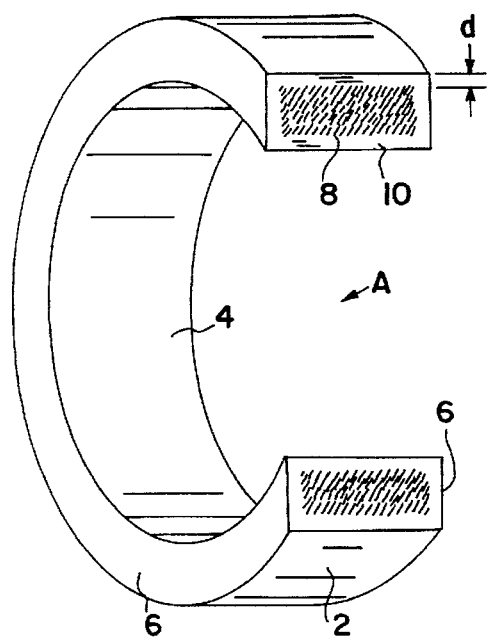
FIG. 1 is a perspective view of a case-carburized ring, partially cut away and in section to show its core and hardened case.

Using the process of the invention, one subjects a steel ring A (FIG. 1) that has been case-carburized to a nondestructive test which reveals the depth at which a selected proportion of carbon exists—all quite quickly and with a reasonable amount of accuracy. The ring A, which may be the race of a typical roller bearing or a so-called carbon cut ring, has an exterior surface 2, an interior surface 4 of lesser diameter, and end surfaces 6 extended radially between the exterior and interior surfaces 2 and 4. At least the exterior surface 2 is continuous in the sense that it is not interrupted by angles. Being case-carburized, the ring A has a core 8 which is relatively ductile and thus able to withstand bending stresses, and a case 10, which is hard and resistant to deformation and wear. The core 8 is formed from low carbon steel or perhaps medium carbon steel, whereas the case 10 is high carbon steel.

The ring A initially has a uniform carbon content, it being that of the core 8. But during the case-carburizing process carbon diffuses into the ring A from the exterior and interior surfaces 2 and 4 and the end surfaces 6, with the depth of the diffusion being dependent on factors such as the carbon content and nature of the carbon-rich atmosphere in which the carburizing occurs, the temperature of the atmosphere, and the time the ring A remains in the atmosphere. Owing to the diffusive character of the process, no well-defined boundary exists between the case 10 and core 8. Instead, the case 10 constitutes a gradient and simply vanishes into the core 8. But the greatest proportion of carbon exists near the surfaces 2, 4 and 6, and to establish a point of reference, some arbitrary carbon content is selected as the boundary between the case 10 and the core 8. Typically, that is 0.5% carbon by weight. Thus, the case 10 has a depth d which is the distance measured perpendicularly from any of its surfaces 2, 4 or 6 to the depth at which 0.5% carbon exists. Of course, in order for the case 10 to transform into the hard martensite, the ring A should be heated to a temperature high enough to convert all of the steel in both the core 8 and the case 10 into austenite. Then the ring A is quenched. A subsequent heating and quenching may follow to temper the steel in the case 10. The heating and quenching and the subsequent tempering constitute a heat treatment for the case-carburized steel.

Through experience one gains a measure of expertise in selecting the duration and atmosphere for producing a desired case depth in a particular steel, but one is never sure, and that is the reason for including the carbon cut ring A with other products that are carburized in a batch. By conducting an Ms test or carbon gradient test on the carbon cut ring A, one can be reasonably assured that the case depth of the carbon cut ring A closely approximates the case depth d for the products of the batch—or one in accordance with the present invention can launch an acoustic surface wave in a selected ring A, measure the velocity at which the wave propagates, compare that velocity with a correlation of velocity and case depth for known rings of the same steel, and thereby derive the case depth.

The velocity of a surface wave in steel depends on a variety of factors including the carbon content, the microstructure (relative amounts of martensite, bainite, pearlite and ferrite), residual stress, and grain size, with the carbon content being by far the most predominant. The higher the carbon content, the slower the wave velocity. Microstructure is perhaps the next in significance. The higher the fraction of martensite, the slower the wave velocity. Thus, a surface wave will propagate more slowly through hard martensite containing a high carbon content than through the softer more ductile ferrite and pearlite, with low carbon content. This variation in velocity is used to establish the depth at which a selected carbon content exists—in short, the case depth d.

In this regard, a surface wave, such as a Rayleigh wave, does not exist wholly at the surface of the medium through which it travels—steel in this instance. On the contrary, the wave, which is actually a disturbance of the medium, exists along the surface where it is most pronounced and the disturbance decreases with depth below the surface. The penetration of the wave extends to a depth of perhaps 0.9 to 1.0 times the wavelength, and of course the wavelength is directly related to frequency. Since a low frequency wave has a greater wavelength than a high frequency wave, the low frequency wave will disturb the steel to a greater depth, or in other words, have a greater penetration depth than the high frequency wave. Because a high frequency surface wave penetrates near the exterior surface and a deep case has a high carbon near the exterior surface, the high-frequency wave will propagate more slowly in a deep case than in a shallow case.

Figure 2:
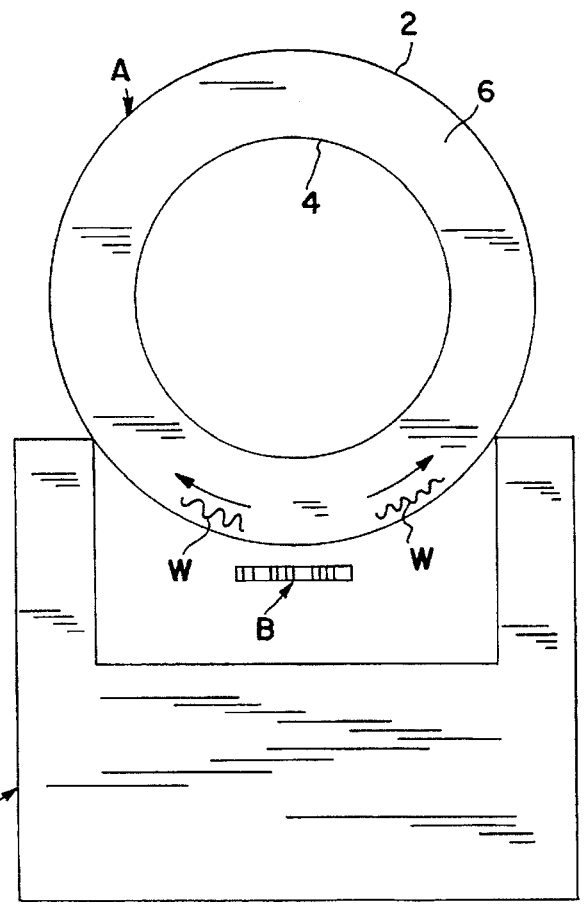
FIG. 2 is a schematic elevational view showing the ring in a fixture which contains an electromagnetic acoustic transducer (EMAT) for launching an acoustic wave in the ring.
Figure 4:
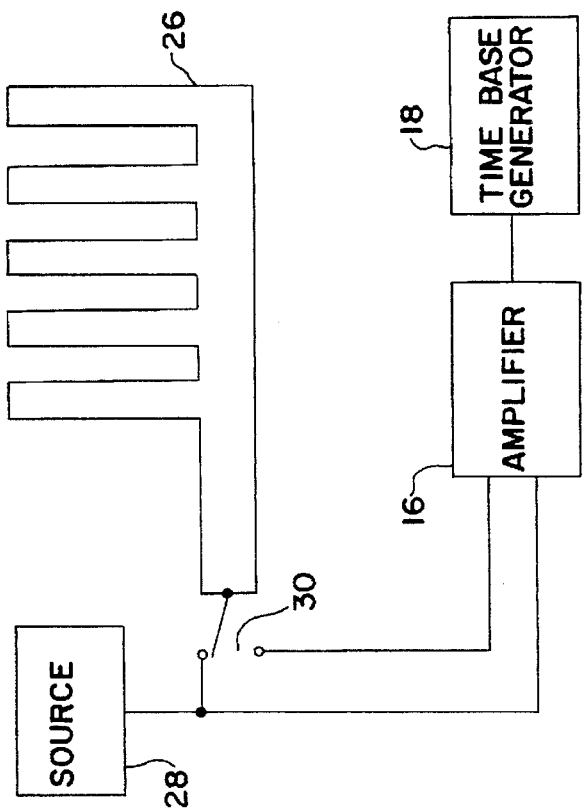
FIG. 4 is a schematic view of the electrical components used to measure the velocity of a wave.

To launch a surface wave in the case-hardened ring A, the ring A is placed in a fixture F (FIG. 2) with one of its surfaces, preferably the exterior surface 2, located adjacent to, but not in contact with, an electromagnetic acoustic transducer B, often referred to as an EMAT, that is within the fixture F. When energized, the EMAT B creates a surface wave in the ring A, and that wave travels circumferentially around the ring A at or below the surface 2 until it attenuates beyond recognition, but usually that is in excess of ten complete turns. With each full turn around the ring A, the wave of course goes by the EMAT B. The EMAT B not only launches the wave, but detects it as well on each of its excursions above the EMAT B. In short, the EMAT B operates on the pulse-echo principle. To this end, immediately after launching the wave, the EMAT B is deenergized and connected with an amplifier 16 (FIG. 4) that is in turn connected to a time base generator 18 such as an oscilloscope. The signal delivered by the amplifier 16 includes spikes which represent the passage of the wave front by the EMAT B, and these spikes will appear as such on the time base generator 18, assuming that it is an oscilloscope. The distance between successive spikes on the time base generator 18 reflects the time for the wave to move once around the exterior surface 2, a length which equals the circumference of the ring A at the exterior surface 2. The circumference divided by the time represents the velocity of the wave. Actually, to achieve better accuracy, the time for multiple revolutions, perhaps as many as ten, is used.

EMATs are conventional devices for producing longitudinal, shear and surface waves. When configured to produce a Rayleigh wave, which is a form of surface wave, the EMAT B has a magnet 20 (FIG. 3), either permanent or electro, with north and south poles 22. In addition, it has a meander coil 26 located generally above one of the poles 22. The meander coil 26 constitutes a current-conducting wire arranged in a zigzag configuration, so as to have successive loops or legs, all located in a single plane—or perhaps in an arc that generally conforms to the exterior surface 2 of the ring A. The coil 26 lies between the magnetic pole 22 and the surface 2 with its legs extending axially with respect to the ring A. The spacing between adjacent legs of the coil 26 remains constant for a given EMAT, and the spacing governs the frequency of wave.

Figure 3:
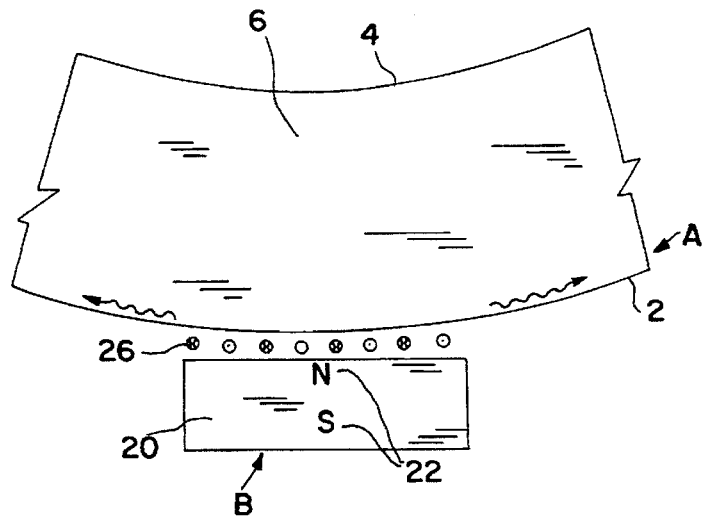
FIG. 3 is a schematic view of the EMAT configured to produce a Rayleigh surface wave and a segment of a ring in which the wave is launched.

In use, the EMAT B is placed along the ring A with the one pole 22 of its magnet 20 presented toward the exterior surface 2, but spaced slightly below the surface 2 (FIG. 3). The meander coil 26 lies even closer to the surface 2, although it too is spaced from the surface 2. The magnet 20 produces a flux which passes through the gap between the pole 22 and the surface 2 and likewise into the ring A beyond the gap. Should the coil 26 be placed across a source 28 (FIG. 4) of alternating current at radio frequency, the current in the coil 26 will induce eddy currents in the ring A directly above the coil 26—and of course within the magnetic field produced by the magnet 20. Indeed, the induced eddy currents interact with the magnetic field to produce Lorentz forces. At any given instant the Lorentz forces for adjacent legs of the coil 26 are in opposite directions; one being directed into the surface 2 and the other directed away from the surface. In other words, the Lorentz force under one leg of the coil 26 pushes the disturbances at surface 2 inwardly, while the Lorentz forces under the adjacent legs pull the disturbance at or below the surface 2 outwardly. Owing to the alternating character of the current in the coil 26, these Lorentz forces are constantly reversing direction, and this excites vibrations in the surface 2 of the ring A, thereby launching a surface wave—indeed, a Rayleigh wave that propagates transversely with respect to the legs of the coil 26 and circumferentially along the surface 2. The spacing between the loops or legs of the coil 26 determines the frequency or wavelength of the Rayleigh wave that is produced.

The Rayleigh wave, once launched, follows the exterior surface 2 of the ring A, passing circumferentially along that surface in both directions. One excursion around the surface 2 brings the wave front back to the EMAT B, and during this interval a switch 30 (FIG. 4) disconnects the coil 26 of the EMAT B from the source 28 and connects it to the amplifier 16. This converts the EMAT B into a detector. The undulating surface in the presence of the magnetic field of the magnet 20 functions much like a coil itself in that it generates current in the surface 2, and that current in turn induces a current in the coil 26 of the EMAT B. This last induced current represents the spikes in the signal which the time base generator 18 displays, assuming it is an oscilloscope. Successive spikes in the display reflect successive passes of the wave front above the EMAT B, and the distance between them represents the time of flight—that is to say, the time it takes the wave front to pass once around the surface.

Once one knows the time for the wave to travel once around the exterior surface 2, it is a simple matter to calculate the wave velocity. It merely represents the distance, in this case the circumference of the surface 2, divided by the time of flight.

$$V\text{wave} = \frac{\text{circumference}}{\text{time for one pass}}$$

Actually, that which is so calculated represents the so-called group velocity of the wave. The Rayleigh wave which is generated inside the ring A by the EMAT B with its meander coil 26 is nearly monochromatic. A monochromatic surface wave undergoes little or no dispersion when it travels through a heterogeneous, medium such as case-carburized steel. Therefore, the monochromatic Rayleigh wave will undergo almost no dispersion as it travels around the ring A, and hence the phase velocity of the wave is approximately equal to its group velocity in this case. Dispersion is present only when a wideband wave propagates in a heterogeneous medium.

In hardened rings A of varying carbon content—and likewise varying martensite content—the velocity varies with the carbon and martensite content. Generally speaking, the higher the carbon content and the greater the martensite, the lower the wave velocity. But without any known correlation between wave velocity and case depth, it is impossible to determine case depth from the measurement of wave velocity. To provide a reference, a number of carbon cut rings, all formed from the same steel are subjected to varying carburizing treatments and then quenched to harden their carburized cases. This produces rings with different depths.

Using the EMAT, the velocity for a Rayleigh surface wave in each ring is determined. Thereupon, the case depth d for each of the rings is determined by one of the traditional procedures, such as the Ms test or the carbon gradient test, with the case depth d being the depth at which a selected proportion of carbon exists. Usually that proportion is 0.5%. This information is plotted on cartesian coordinates to produce a graph (FIG. 5), the velocity being along one axis and case depth along the other. The plots establish a curve for correlating velocity with case depth. But each curve is specific to a particular steel, a particular frequency, a particular heat treatment and a particular coil 26. Thus, for any EMAT B, which has a specific spacing in its coil 26, curves must be constructed for all the steels one expects to examine at the frequency for that coil.

To determine the case depth of an unexamined ring A which has undergone case-carburizing and hardening, the exterior surface 2 of the ring A is placed along the magnetic pole 22 and coil 26 of the EMAT B. When energized, the EMAT B launches a Rayleigh wave along the surface 2 of the ring A and further detects the wave front as it thereafter passes the EMAT B on its several excursions around the surface 2. The measurements derived from the EMAT B provide the wave velocity. Using the graph (FIG. 5) and curve that are specific to the steel in the core 8 of the ring A and the heat treatment and the frequency, one finds the case depth which correlates with that wave velocity. That is, of course, the depth d of the case 10 for the ring A under consideration.

Where like rings A are carburized in a single batch and subjected to identical heat treatments, only a few of the rings A need be examined using EMAT B and the procedure described. Since the examined rings A are not in any way damaged, they are well-suited for their intended use, whether it be that of a bearing race or some other machine component. Or a batch of products may include a carbon cut ring A which undergoes the carburizing and hardening, as in the past. Only the carbon cut ring A is evaluated. However, instead of being subjected to one of the destructive tests, a Rayleigh wave is generated in the ring A and measured to determine the velocity of the wave, and from that velocity the depth d of its case 10 is determined.

EXAMPLE

Forty carbon cut rings A, each having an outside diameter of 2 inches and an inside diameter of 1 inch, were divided into 10 groups, with each group containing four rings A. Not only were the rings A identical in size, but each was formed from the same steel, that is AISI 8119 which is commonly found in case-carburized bearing races and rollers. It contains 0.19% carbon by weight. While the carburizing treatment was the same for each of the four specimens in any group, it varied among groups. Each group of four rings A underwent a different carburizing treatment or cycle. By reason of the carburizing treatments, the rings A acquired carburized cases 10, with the depths d of the cases 10 for the rings A of any group being essentially the same, but of course the depths d varying from group to group. Actually, the rings A of one of the groups, although having undergone a treatment, did not acquire carburized cases 10 since the atmosphere in which that treatment occurred contained no carbon. The rings A of this group served as controls. All of the rings A were then subjected to identical heat treatments.

At the completion of the carburized and heat treatments, one ring A from each group was removed, cut into four segments. Using the Ms test, two of the segments were measured for the depth d at which 0.5% carbon existed and the other two were used to measure the depth d at which 0.8% carbon existed. The following table describes the treatments and results in more detail:

at the 0.5% carbon level and the 0.8% carbon level. The remaining rings A for each group were subjected to the nondestructive acoustic tests to determine the velocities at which they transmitted surface waves. Along each remaining ring A the EMAT B was placed and energized at several different frequencies, namely 500 KHz, 750 KHz and 1000 KHz. The coil 26 of the EMAT B had its legs or loops spaced apart a distance compatible with the frequency of the current impressed upon it. For 500 KHz, it equaled 3 mm; for 750 KHz, 2 mm; and for 1000 KHz, 1.5 mm. Each ring A yielded a velocity for the surface wave generated by the EMAT B. The following table gives the results:

| Group | Case Depth (in) 0.5% C | Average Velocity (m/s) 500 KHz | Average Velocity (m/s) 750 KHz | Average Velocity (m/s) 1000 KHz |
| --- | --- | --- | --- | --- |
| 1 | 0 | 2976.60 | 2971.56 | 2971.14 |
| 2 | .0415 | 2953.01 | 2930.59 | 2920.76 |
| 3 | .0315 | 2961.29 | 2943.51 | 2932.83 |
| 4 | .04 | 2954.28 | 2932.31 | 2923.54 |
| 5. | .048 | 2947.73 | 2924.53 | 2918.25 |
| 6. | .052 | 2942.08 | 2923.13 | 2920.27 |
| 7. | .064 | 2937.39 | 2918.44 | 2917.48 |
| 8. | .085 | 2920.77 | 2912.37 | 2913.63 |
| 9. | .0975 | 2919.54 | 2914.14 | 2915.19 |
| 10. | .069 | 2928.69 | 2912.46 | 2911.30 |

Figure 5:
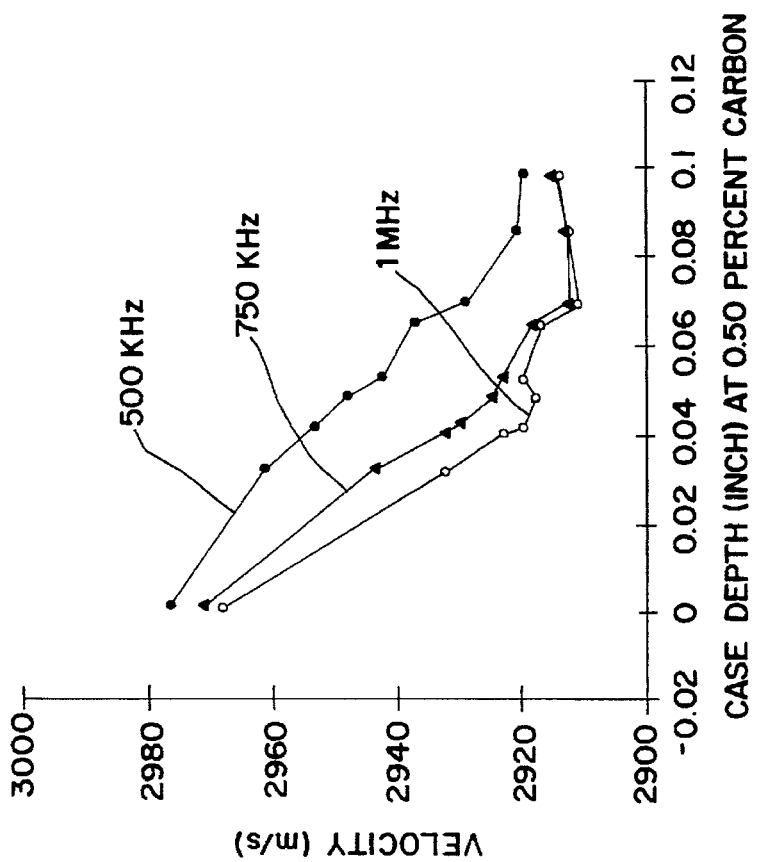
FIG. 5 is a graph showing the correlation between case depth and the velocity of a generally monochromatic surface wave for several frequencies imparted to the coil of the EMAT.

The foregoing velocities, when plotted on Cartesian coordinates against the case depths with which they corresponded, yielded a graph containing three curves—one for each frequency (FIG. 5).

The graph (FIG. 5) derived from the velocity measurements reveals a more uniform relationship between velocity and case depth at lower frequencies impressed upon the meander coil 26 of the EMAT B than at higher frequencies, at least in the region of deeper case depths. This stands to reason, because a low frequency surface wave has a higher wavelength than a high frequency surface wave, and since the depth of penetration approximates wavelength, the low frequency surface wave will have a greater penetration. In contrast, the high frequency surface waves, 750 KHz, 1000 KHz, penetrate the rings A only near their exterior surfaces 2 and may not penetrate cases 10 of deeper case depth. And, the low frequency surface waves of 500 KHz penetrates beyond the case region in the specimen. Hence, the curve for

| | | Carburizing Treatment | | | | Case Depth (average) | |
| --- | --- | --- | --- | --- | --- | --- | --- |
| Group | Temp. °F. | Time in carbon atmos. (hours) | O₂ probe setting (mv) | Time Diffuse in N₂ (hours) | Quench temp. °F. | 0.5% carbon (in) | 0.8% carbon (in) |
| 1. | 1750 | 6 | —no carbon— | | | 0 | 0 |
| 2. | 1750 | 6 | 1180 | 1.0 | oil at 140 | .0415 | .018 |
| 3. | 1750 | 3 | 1180 | .5 | oil at 140 | .0315 | .015 |
| 4. | 1700 | 7 | 1190 | 1.0 | oil at 140 | .040 | .019 |
| 5. | 1700 | 9 | 1190 | 1.0 | oil at 140 | .048 | .029 |
| 6. | 1700 | 18 | 1173 | 2.0 | oil at 140 | .052 | .008 |
| 7. | 1700 | 24 | 1173 | 2.0 | oil at 140 | .064 | .021 |
| 8. | 1700 | 25 | 1190 | 3.0 | oil at 140 | .085 | .054 |
| 9. | 1750 | 25 | 1190 | 3.0 | oil at 140 | .0975 | .0615 |
| 10. | 1700 | 22 | 1190 | 2.0 | oil at 140 | .069 | .041 |

The Ms tests for the one ring A of each group determined the case depth d for the remaining rings A of the group, both the surface waves at 500 KHz displays a generally uniform character—indeed, approaching linearity—even at deep case depths, while the curves at 750 and 1000 KHz display erratic changes at higher case depths.

Of course similar graphs may be produced for other steels and such graphs provide a basis for determining the case depth of other rings. To be sure, one must know the steel from which these rings are formed, that is the steel in their cores 8, and also the heat treatments to which the carburized steels have been subjected, for each curve is specific to a particular steel and heat treatment. Once the velocity for the ring A of unknown case depth d is determined, one simply goes to the correlation graph for that steel and heat treatment and, using the curve for the frequency at which the test was conducted, compares the measured velocity with the appropriate curve to determine the case depth. But one must insure that the EMAT B used to establish the graph and the EMAT B used for the tests are identical in the sense that both EMATs have the same frequency and other similar characteristics. In short, the graphs and their curves enable one to ascertain case depths for any velocity by making a simple comparison.

Another option, one can obtain several correlation curves between velocity and case depth at different frequencies using a single wideband EMAT/or a wideband transducer. (A wideband transducer generates waves that contain many frequencies.) However when a wideband surface wave propagates in a dispersive or heterogeneous medium such as case carburized component, the wave velocity is a function of frequency or wavelength, and the group velocity is significantly different from the phase velocity. It is, therefore, important to study the variation of phase velocity, instead of group velocity, with case depth at different frequencies. The variation of phase velocity with case depth for various frequencies can be performed by using either a wideband EMAT or a wideband wedge transducer as a transmitter and two wideband EMATs or wideband knife edge transducers as receivers. The wideband wedge transducer or EMAT transmits surface waves with different frequency components in a case carburized component. The two wideband receivers are located as positions X1 and X2 and receive the waves which arrive at the receivers at different times. The distance between the two EMATs or two knife-edge transducers is permanently fixed. When any wave is received at each position, it is converted from the time domain to the frequency domain using a Fourier Transform (FFT). The phase velocity at each frequency f is then computed by multiplying the angular frequency $\omega$ with the distance traveled by the wave between the two receivers $(x_2-x_1)$ and then dividing by the phase difference of the two waves received $(\Phi_2-\Phi_1)$. This calculation is illustrated in the following equation:

$$V_{phase}=(x_2-x_1)(\omega)/(\Phi_2-\Phi_1)$$

where $\omega=2(\pi f)$

Figure 6:
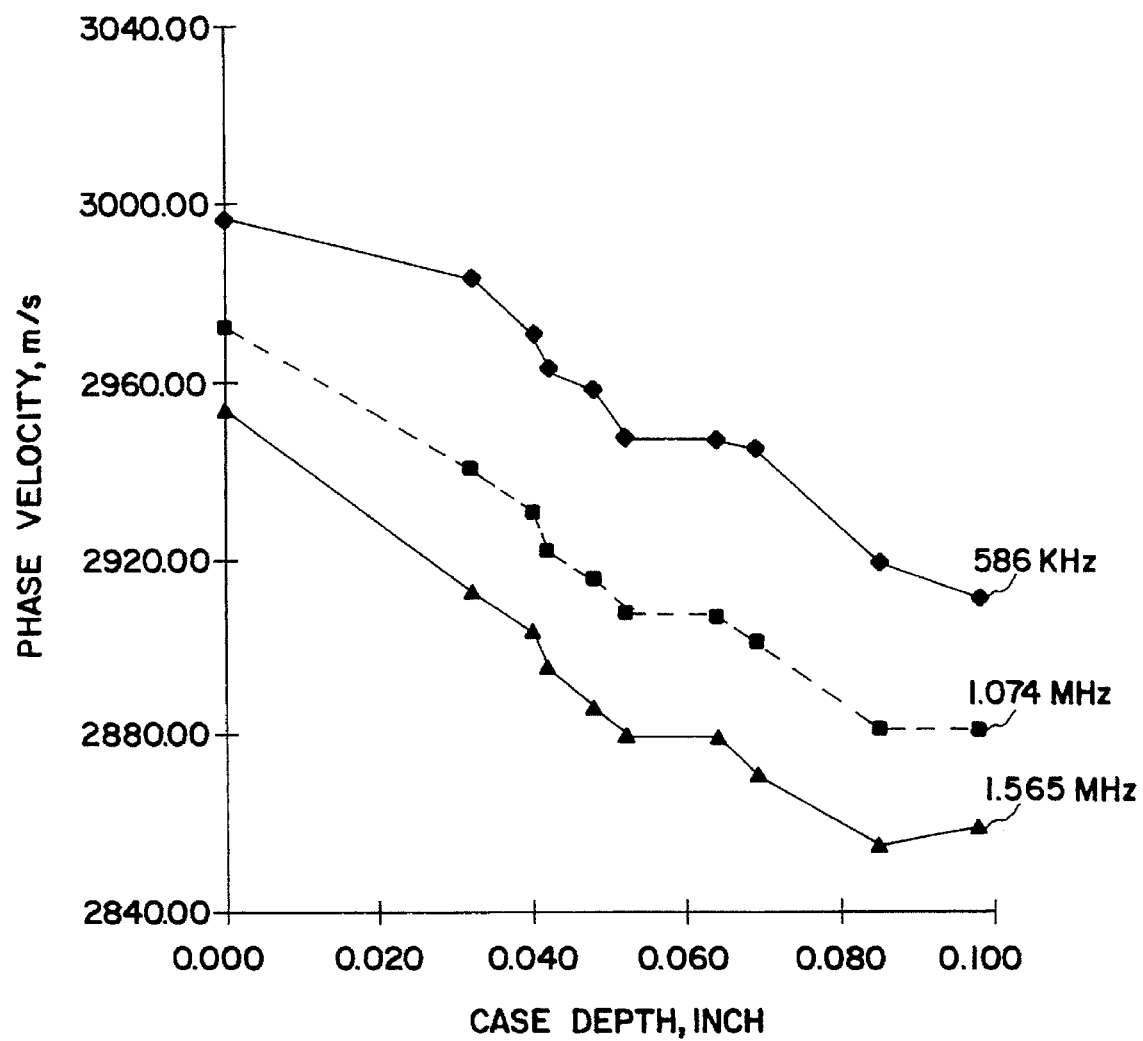
FIG. 6 is a graph showing the correlation between phase velocity and case depth for various frequencies of the wideband transducer.

The phase velocity is calculated at each case depth in the same manner and plotted as a function of case depth for each frequency. The resulting curves between phase velocity and case depths for varying frequencies (FIG. 6) refer to phase velocity curve which occurs since the surface wave is not monochromatic and is propagated in a heterogeneous case carburized specimen which has material properties which vary with depth. In this way, one can generate several curves for different frequencies with a single EMAT in use.

Group velocity of course represents distance per unit of time. If the distance does not vary between the rings A used to construct the graphs and the ring A of unknown case depth, one only needs to compare time to determine case depth, for in that situation time and group velocity are in effect equivalent.

This invention is intended to cover all changes and modifications of the example of the invention herein chosen for purposes of the disclosure which do not constitute departures from the spirit and scope of the invention.

What is claimed is:

1. A process for nondestructively determining the case depth of a specimen of steel which is case-carburized, so as to have a core and a case of higher carbon content than the core, with the case depth being the distance from a surface of the specimen to a location in the specimen at which a prescribed content of carbon exists in the specimen, said process comprising: launching an acoustic wave along the surface of the specimen at a predetermined frequency such that the acoustic wave passes through the case; measuring the velocity of the acoustic wave in the specimen; and comparing the measured velocity of the acoustic wave with a correlation previously established between velocity and case depth, at the predetermined frequency and for the same type of steel as that of the specimen, to determine the case depth that corresponds to the measured velocity of the acoustic wave.

2. The process according to claim 1 and further comprising establishing a correlation between velocity and case depth for the steel.

3. The process according to claim 1 wherein the specimen is a ring having a peripheral surface, and the acoustic wave propagates along the peripheral surface of the ring.

4. The process according to claim 1 wherein the specimen has a continuous peripheral surface that is free of angles, and the step of launching the acoustic wave includes positioning an EMAT along the peripheral surface of the specimen, with the EMAT having a coil; and energizing the coil of the EMAT with a high frequency electrical current, such that the EMAT disturbs the peripheral surface.

5. The process according to claim 4 wherein the step of measuring the velocity of the acoustic wave includes detecting the presence of the acoustic wave in the peripheral surface with the EMAT and measuring the time for the acoustic wave to pass from the EMAT back to the EMAT.

6. The process according to claim 4 wherein the EMAT is configured and located to launch a surface wave which travels along the peripheral surface of the specimen from the location of the EMAT back to that location.

7. The process according to claim 6 wherein the step of measuring the velocity of the acoustic wave includes measuring the time for the acoustic wave to complete several excursions around the peripheral surface.

8. The process according to claim 7 wherein the frequency of the acoustic wave is such that the acoustic wave penetrates the specimen to a depth at least as great as that of the case depth.

9. A process for measuring case depth in terms of the depth at which a prescribed carbon content exists in a steel ring that is case-carburized and has a continuous peripheral surface, said process comprising: positioning an EMAT along the peripheral surface with the EMAT having a coil arranged to produce a surface wave in the ring; energizing the coil of the EMAT with an electrical current at a predetermined frequency such that a surface wave is launched in the peripheral surface of the ring; with the EMAT, detecting the presence of the surface wave at a location from which the surface wave was launched; measuring the velocity of the surface wave; and comparing the measured velocity of the surface wave with an existing correlation of velocity and case depth at the predetermined frequency and for the same type of steel as that of the ring to determine the case depth that corresponds to the measured velocity of the surface wave.

10. The process according to claim 9 wherein the step of measuring the velocity of the wave includes measuring the time for the wave to pass several times around the peripheral surface.

11. The process according to claim 9 wherein the wavelength of the wave is such that the wave penetrates the ring to a depth at least as great as the measured case depth.

12. A process for nondestructively determining the case depth for a specimen of case-hardened steel, which has a core and a case, to determine the depth of the case in terms of the distance from the surface of the specimen to a location in the specimen at which a prescribed content of carbon exists in the specimen, said process comprising: launching an acoustic wave in the specimen with an EMAT at a predetermined frequency such that the wave passes through the case and along the surface of the specimen; measuring the velocity of the acoustic wave in the specimen; and comparing the measured velocity of the acoustic wave with an established correlation between velocity and case depth in terms of carbon content for the same steel as that of the specimen and at the frequency to determine the case depth that corresponds to the measured velocity of the acoustic wave.

* * * * *